United States Patent [19]

Peyman et al.

[11] Patent Number: 5,608,098

[45] Date of Patent: Mar. 4, 1997

[54] BIS(AMINOMETHYL)PHOSPHINIC ACID DERIVATIVES AND PROCESS FOR THE PREPARATION OF BIS(AMINOMETHYL)PHOSPHINIC ACID DERIVATIVES

[75] Inventors: Anuschirwan Peyman, Kelkheim; Jörg Spanig, Berlin; Karl-Heinz Budt, Kelkheim, all of Germany

[73] Assignee: Hoechst Aktiengesellschaft, Frankfurt am Main, Germany

[21] Appl. No.: 525,787

[22] PCT Filed: Mar. 24, 1994

[86] PCT No.: PCT/EP94/00950

§ 371 Date: Sep. 28, 1995

§ 102(e) Date: Sep. 28, 1995

[87] PCT Pub. No.: WO94/22879

PCT Pub. Date: Oct. 13, 1994

[30] Foreign Application Priority Data

Apr. 2, 1993 [DE] Germany .................. 43 10 815.6

[51] Int. Cl.$^6$ .................. C07F 9/30; C07F 9/32; C07F 9/38; C07F 9/40
[52] U.S. Cl. .................. 558/145; 558/155; 558/158; 558/159
[58] Field of Search .................. 558/145

[56] References Cited

U.S. PATENT DOCUMENTS 5,099,063  3/1992  Parsons et al. .

FOREIGN PATENT DOCUMENTS

| 0435059A1 | 7/1991 | European Pat. Off. . |
| 2805074A1 | 8/1978 | Germany . |
| 3824961A1 | 1/1990 | Germany . |
| WO93/20086 | 10/1993 | WIPO . |

OTHER PUBLICATIONS

Schrader, T. et al. "Synthese von 1–Aminophosphonäure –Derivaten über Acyliminophosphonsäure–Ester" Synthesis 1986, (5), 372–375.

Schrader, T. et al. "Phosphoranaloge von Aminosäuren IV. Synthesen ungewöhnlicher 1–Aminophosphonsäuren über Diels–Alder Reaktionen von (N–Acyliminomethyl)phosphonsäurediethylestern" Synthesis 1990, (12), 1153–1156.

Primary Examiner—Johann Richter
Assistant Examiner—Michael G. Ambrose
Attorney, Agent, or Firm—Finnegan, Henderson, Farabow, Garrett & Dunner, L.L.P.

[57] ABSTRACT

Novel bis(aminomethyl)phosphinic acid derivatives and process for the preparation of bis(aminomethyl)phosphinic acid derivatives Compounds of the formula VI

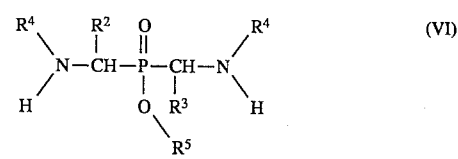

can be prepared by reaction of a compound of the formula IV

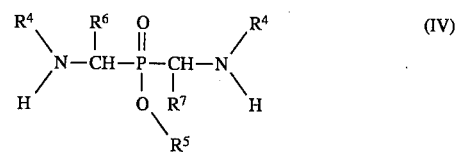

with a base to give a compound of the formula Va or Vb

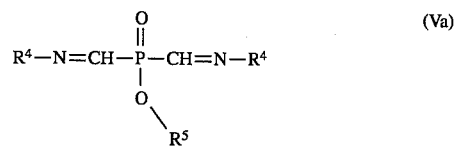

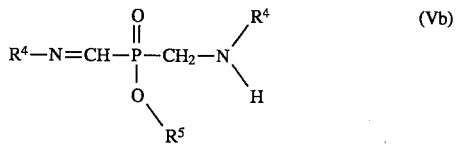

and subsequent reaction with carbon nucleophiles; alternatively the compound of the formula VI is prepared by direct reaction of the compound of the formula IV e.g. with $R^2Cu(CN)Li_2$, the above substituents having the meanings mentioned.

8 Claims, No Drawings

BIS(AMINOMETHYL)PHOSPHINIC ACID DERIVATIVES AND PROCESS FOR THE PREPARATION OF BIS(AMINOMETHYL)PHOSPHINIC ACID DERIVATIVES

This application was filed under 35 U.S.C. §371 and was based upon PCT International Application No. PCT/EP94/00950, filed Mar. 24, 1994.

BACKGROUND OF THE INVENTION

1. Description of the Related Art

α-Aminophosphonic acids and their derivatives are gaining greater and greater importance, e.g. as enzyme inhibitors, in biochemistry, pharmaceutical chemistry and in the field of plant protection [P. Kafarski, B. Lejczak, Phosph., Sulfur, and Silicon, 63 (1991)193]. There is a whole range of processes for the synthesis of this class of compound, which have been summarized in various reports [Kukhar and Solodenko, Russ. Chem. Rev. 56 (1987) 859, Redmoore, Topics in Phosphorus Chemistry, Vol. 11, Grayson and Griffith, Ed., Wiley 1976, 515].

The preparation of another class of compound, bis(aminomethyl)phosphinic acid and its derivatives, which are likewise of increasing importance in pharmaceutical chemistry (EP 0435059 A1), is far more complicated and only documented to a small extent. The synthesis of the parent compound was described for the first time by Meier [L. Meier, J. Organomet. Chem. 178 (1979) 157, DE 2805074A1, see also Kober et al., DE 3824961A1]. One possibility for the preparation of α- or α,α'-substituted derivatives of bis(aminomethyl)phosphinic acid is described by Tyka et al. [Phosphorus, Sulfur, and Silicon 62 (1991) 75]. The method is based on the addition of hypophosphorous acid to Schiff bases with formation of aminoalkylphosphonous acids in the first step, which are then reacted in the following step with arylidene bisamides to give α,α-bis(aminoalkyl)phosphinic acids. This process, however, is limited to the reaction with arylidene bisamides and is furthermore characterized by moderate yields. Only moderate yields were also observed for the double addition of hypophosphorous acid to Schiff bases with the formation of α,α'-bis(aminoalkyl)phosphinic acids. A further process [A. Peyman et al., Tetrahedron Lett. 33 (1992) 4549] is based on the alkylation of bis(aminomethyl)phosphinic acid, but in this way only radicals can be introduced which are accessible to nucleophilic substitution. Surprisingly, it has been found that many compounds can be prepared advantageously by alkylations of reverse polarity.

2. Summary of the Invention

The invention accordingly relates to a process for the preparation of compounds of the formula VI

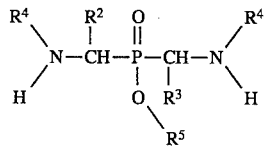

in which $R^2$ and $R^3$, independently of one another, are hydrogen, $(C_1-C_{18})$-alkyl, $(C_2-C_{18})$-alkenyl, $(C_2-C_{18})$-alkynyl, where alkyl, alkenyl and alkynyl can in each case be substituted one or more times by fluorine, chlorine, bromine, COOH, oxo, $NO_2$, $NH_2$, NHC(O)—$(C_1-C_6)$-alkyl, NHC(O)—$(C_6-C_{12})$-aryl, CN, OH, CHO, CH—[$(C_1-C_6)$-alkoxy]$_2$, COOH, $SO_3H$, C(O)—O—$(C_1-C_6)$-alkyl, C(O)—O—$(C_6-C_{12})$-aryl, C(O)—$(C_1-C_6)$-alkyl, C(O)—$(C_6-C_{12})$-aryl, O—C(O)—$(C_1-C_6)$-alkyl, O—C(O)—$(C_6-C_{12})$-aryl, $(C_1-C_6)$-alkoxy, are $(C_6-C_{12})$-aryl, $(C_7-C_{22})$-arylalkyl, where aryl can be substituted one or more times by fluorine, chlorine, bromine, $NO_2$, $NH_2$, NHC(O)—$(C_1-C_6)$-alkyl, NHC(O)—$(C_6-C_{12})$-aryl, CN, OH, COOH, $(C_1-C_6)$-alkyl, $(C_1-C_6)$-alkoxy, C(O)—O—$(C_1-C_6)$-alkyl, C(O)—O—$(C_6-C_{12})$-aryl, C(O)—$(C_1-C_6)$-alkyl, C(O)—$(C_6-C_{12})$-aryl, O—C—(O)—$(C_1-C_6)$-alkyl, O—C(O)—$(C_6-C_{12})$-aryl, or are $P(O)[OH]_2$, $P(O)(OR^{23})_2$, where $R^{23}$ independently of one another is $(C_1-C_6)$-alkyl, $(C_6-C_{12})$-aryl or $(C_7-C_{13})$-arylalkyl and where aryl can be substituted one or more times by fluorine, chlorine, bromine, $NO_2$, CN, OH, COOH, $(C_1-C_6)$-alkyl, $(C_1-C_6)$-alkoxy, C(O)—O—$(C_1-C_6)$-alkyl, C(O)—O—$(C_6-C_{12})$-aryl, C(O)—$(C_1-C_6)$-alkyl, C(O)—$(C_6-C_{12})$-aryl, O—C(O)—$(C_1-C_6)$-alkyl or O—C(O)—$(C_6-C_{12})$-aryl, where $R^2$ and $R^3$ are not simultaneously hydrogen, $R^4$ is a protective group for the amino function and $R^5$ is $(C_1-C_{18})$-alkyl, $(C_2-C_{18})$-alkenyl, $(C_2-C_{18})$-alkynyl, $(C_6-C_{12})$-aryl, $(C_7-C_{20})$-arylalkyl, where alkyl, alkenyl, alkynyl and aryl can be substituted one or more times by fluorine, chlorine, bromine, oxo, $NO_2$, $NH_2$ or protected form, CN, OH, COOH, $(C_1-C_6)$-alkyl, $(C_1-C_6)$-alkoxy, C(O)—O—$(C_1-C_6)$-alkyl, C(O)—O—$(C_6-C_{12})$-aryl, C(O)—$(C_1-C_6)$-alkyl, C(O)—$(C_6-C_{12})$-aryl, O—C(O)—$(C_1-C_6)$-alkyl, O—C(O)—$(C_6-C_{12})$-aryl, which comprises converting a compound of the formula IV

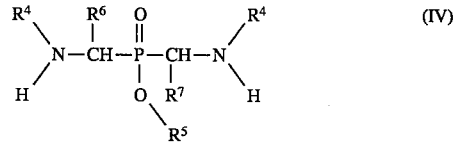

in which $R^4$ and $R^5$ have the abovementioned meaning and $R^6$ and $R^7$ independently of one another are H, Cl or Br, where not both radicals are simultaneously hydrogen a) by reaction with a base to a compound of the formula Va or Vb

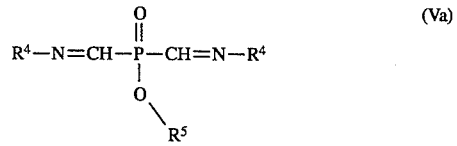

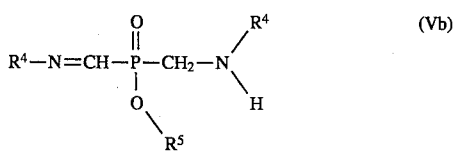

where $R^4$ and $R^5$ have the abovementioned meanings and for the preparation of the compound VI a compound of the formula Va or Vb is reacted with carbon nucleophiles, or b) the compound of the formula VI is prepared by direct reaction of a compound of the formula IV with $R^2_2Cu(CN)Li_2$, $R^2Li$, $R^2MgX$, $R^2ZnX$, $R^2_2Zn$, $R^2_{4-n}TiR^{22}_n$ (n<4) $P[O—R^{23}]_3$, where $R^2$ has the abovementioned meaning, $R^{22}$ is N—[$(C_1-C_6)$-alkyl]$_2$, O—$(C_1-C_6)$-alkyl, O—$(C_6-C_{12})$-aryl, where aryl can be substituted by fluorine, chlorine, bromine, $NO_2$ $NH_2$ or protected form, CN, OH, COOH, C(O)—O—$(C_1-C_6)$-alkyl, $(C_1-C_6)$-alkyl, $(C_1-C_6)$-alkoxy, or is a tartaric acid derivative and $R^{23}$ is $(C_1-C_6)$-alkyl, $(C_6-C_{12})$-aryl, $(C_7-C_{13})$-arylalkyl, where aryl can be substituted one or more times by fluorine, chlorine, bromine, $NO_2$, CN, OH, COOH, ($C_1$–$C_6$)-alkyl, ($C_1$–$C_6$)-alkoxy, C(O)—O—($C_1$–$C_6$)-alkyl, C(O)—($C_1$–$C_6$)-alkyl, O—C(O)—($C_1$–$C_6$)-alkyl, and X is a leaving group.

DESCRIPTION OF THE PREFERRED EMBODIMENTS

The process for the preparation of compounds of the formula VI is particularly suitable in which $R^2$ and $R^3$ independently of one another are ($C_1$–$C_6$)-alkyl, ($C_2$–$C_6$)-alkenyl, ($C_2$–$C_6$)-alkynyl, where alkyl can be substituted one or more times by oxo, fluorine, chlorine, bromine, COOH, C(O)—($C_1$–$C_6$)-alkyl, C(O)—O—($C_1$–$C_6$)-alkyl, ($C_6$–$C_{12}$)-aryl, ($C_7$–$C_{13}$)-arylalkyl, where aryl can be substituted one or more times by chlorine, bromine, CN, ($C_1$–$C_3$)-alkoxy; P(O)[OH]$_2$, P(O)(OR$^{23}$)$_2$, where $R^{23}$ independently of one another is ($C_1$–$C_6$)-alkyl, ($C_6$–$C_{12}$)-aryl or ($C_7$–$C_{13}$)-arylalkyl, in particular $R^1$ and $R^2$ are ($C_1$–$C_6$)-alkyl, ($C_2$–$C_6$)-alkenyl, ($C_2$–$C_6$)-alkynyl, benzyl, P(O)[OH]$_2$ or P(O)[O—($C_1$–$C_6$)-alkyl]$_2$, and $R^5$ is ($C_1$–$C_4$)-alkyl, ($C_2$–$C_4$)-alkenyl, phenyl, benzyl, in particular $R^5$ is ($C_1$–$C_4$)-alkyl or benzyl.

The imines Va are prepared by the reaction of IV ($R^6$ and $R^7$=halogen) with 1 to 10 equivalents, preferably 2 to 2.2 equivalents, of base, preferably tri-($C_1$–$C_6$)-alkylamine, pyridine, butyllithium, lithium diisopropylamide (LDA), sodium hydride, sodium amide, potassium tert-butoxide or complex bases such as sodium amide-R$^{21}$ONa, where $R^{21}$ is ($C_2$–$C_6$)-alkyl or $CH_3CH_2$—O—$CH_2CH_2$ or uncharged, peralkylated polyaminophosphazene bases [R. Schwesinger, H. Schlemper, Angew. Chem. 99(1987)1212; R. Schwesinger, Nachr. Chem. Tech. Lab. 38 (1990)1214], preferably with trialkylamines, pyridine, in a suitable organic solvent, preferably tetrahydrofuran (THF), diethyl ether (ether) or dichloromethane, at a temperature from –120° to 50° C., preferably –100° to 0° C. The highly reactive compounds of the formula V are preferably employed without further purification, optionally after filtration. The imines Vb can also be prepared according to the method described above. However, in the reaction of the monosubstituted compounds IV ($R^7$=H), only 0.5 to 5 equivalents, preferably 1 to 1.1 equivalents, of the above-mentioned bases are used.

The bis(iminomethyl)phosphinic acid esters V are then reacted to give α,α'-substituted phosphinic acid esters VI.

$R^4$ and $R^5$ are defined as described above.

$e_1$) For the preparation of compounds of the formula VI ($R^3$=$R^2$), the bis(iminomethyl)phosphinic acid ester Va is reacted with 1 to 10 equivalents, preferably 2 to 2.2 equivalents, of carbon nucleophiles which are generated from CH-acidic compounds such as e.g. VIIa and VIIb, VIII, IX by bases such as butyllithium, LDA, sodium hydride, sodium amide, potassium tert-butoxide, complex bases (sodium amide-R$^{21}$ONa) or the like, of the organometallic compounds $R^{22}$Cu(CN)Li$_2$, $R^2$Li, $R^2$MgX, $R^2$ZnX, $R^2{}_2$Zn or $R^2{}_{4-n}$TiR$^{22}{}_n$ (n<4), preferably nucleophiles from VII, VIII, IX, $R^2{}_2$Cu(CN)Li$_2$, $R^2$MgX in a suitable solvent preferably THF, ether, at a temperature from –120° to 150° C., preferably –100° to 0° C.

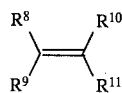 VII

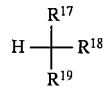 VIII

 IX

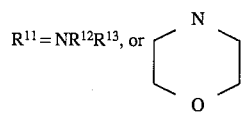 a

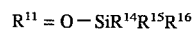 b $R^2$ and $R^{22}$ are as defined above, but are not hydrogen, and X is a leaving group, preferably chlorine, bromine, iodine, O-p-toluenesulfonate, O-trifluoromethylsulfonate, O—($C_1$–$C_6$)-alkylsulfonate, particularly preferably chlorine, bromine, iodine.

Tartaric acid derivatives suitable for the reaction are described in D. Seebach et al. [Tetrahedron 48 (1992) 5719].

$R^8$, $R^9$, $R^{10}$, identically to or independently of one another, are hydrogen, ($C_1$–$C_{18}$)-alkyl, ($C_2$–$C_{18}$)-alkenyl, ($C_2$–$C_{18}$)-alkynyl, ($C_6$–$C_{12}$)-aryl, ($C_7$–$C_{20}$)-arylalkyl. In this case alkyl, alkenyl, alkynyl and aryl can be substituted one or more times by fluorine, chlorine, bromine, $NO_2$, $NH_2$ or protected form [Greene, Protective Groups in Organic Synthesis, Wiley 1979], ($C_1$–$C_6$)-alkyl, ($C_1$–$C_6$)-alkoxy, CN, OH, CHO, CH—[($C_1$–$C_6$)-alkoxy]$_2$, COOH, C(O)—O—($C_1$–$C_6$)-alkyl, C(O)—O—($C_6$–$C_{12}$)-aryl, C(O)—($C_1$–$C_6$)-alkyl, C(O)—($C_6$–$C_{12}$)-aryl, O—C(O)—($C_1$–$C_6$)-alkyl, O—C(O)—($C_6$–$C_{12}$)-aryl.

$R^{12}$, $R^{13}$, $R^{14}$, $R^{15}$ and $R^{16}$ are identical to or independent of one another and are ($C_1$–$C_6$)-alkyl, ($C_6$–$C_{12}$)-aryl, where alkyl and aryl can be substituted one or more times by fluorine, chlorine, bromine, $NO_2$, $NH_2$ or protected form, CN, OH, COOH, ($C_1$–$C_6$)-alkyl, ($C_1$–$C_6$)-alkoxy, C(O)—O—($C_1$–$C_6$)-alkyl, C(O)—O—($C_6$–$C_{12}$)-aryl, C(O)—($C_1$–$C_6$)-alkyl, C(O)—($C_6$–$C_{12}$)-aryl, O—C(O)—($C_1$–$C_6$)-alkyl, O—C(O)—($C_6$–$C_{12}$)-aryl.

$R^{17}$ is hydrogen, ($C_1$–$C_6$)-alkyl, where alkyl can be substituted one or more times by fluorine, chlorine, bromine, $NO_2$, $NH_2$ or protected form, CN, OH, COOH, ($C_1$–$C_6$)-alkyl, ($C_1$–$C_6$)-alkoxy, C(O)—O—($C_1$–$C_6$)-alkyl, C(O)—O—($C_6$–$C_{12}$)-aryl, C(O)—($C_1$–$C_6$)-alkyl, C(O)—($C_6$–$C_{12}$)-aryl, O—C(O)—($C_1$–$C_6$)-alkyl, O—C(O)—($C_6$–$C_{12}$)-aryl.

$R^{18}$ and $R^{19}$, identically to or independently of one another, are hydrogen, CN, C(O)—O—($C_1$–$C_6$)-alkyl, C(O)—O—($C_6$–$C_{12}$)-aryl, C(O)—($C_1$–$C_6$)-alkyl, C(O)—($C_6$–$C_{12}$)-aryl, where alkyl and aryl can be substituted one or more times by fluorine, chlorine, bromine, $NO_2$, $NH_2$ or protected form, CN, OH, COOH, ($C_1$–$C_6$)-alkyl, ($C_1$–$C_6$)-alkoxy, C(O)—O—($C_1$–$C_6$)-alkyl, C(O)—O—($C_6$–$C_{12}$)-aryl, C(O)—($C_1$–$C_6$)-alkyl, C(O)—($C_6$–$C_{12}$)-aryl, O—C(O)—($C_1$–$C_6$)-alkyl, O—C(O)—($C_6$–$C_{12}$)-aryl, with the proviso that for $R^{18}$=hydrogen, $R^{19}$ cannot also be hydrogen and conversely.

$R^{20}$ is hydrogen, ($C_1$–$C_{18}$)-alkyl, ($C_2$–$C_{18}$)-alkenyl, ($C_2$–$C_{18}$)-alkynyl, ($C_6$–$C_{12}$)-aryl, ($C_7$–$C_{20}$)-arylalkyl. In this case alkyl, alkenyl, alkynyl and aryl can be substituted one or more times by fluorine, chlorine, bromine, $NO_2$, $NH_2$ or protected form, [Greene, Protective Groups in Organic Synthesis, Wiley 1979], ($C_1$–$C_6$)-alkyl, ($C_1$–$C_6$)-alkoxy, CN, OH, CHO, CH—[($C_1$–$C_6$)-alkoxy]$_2$, COOH, C(O)—O—($C_1$–$C_6$)-alkyl, C(O)—O—($C_6$–$C_{12}$)-aryl, C(O)—($C_1$–$C_6$)-alkyl, C(O)—($C_6$–$C_{12}$)-aryl, O—C(O)—($C_1$–$C_6$)-alkyl, O—C(O)—($C_6$–$C_{12}$)-aryl. After working up and purification by concentration, e.g. crystallization, extraction, purification on silica gel, the compounds VI ($R^2$=$R^3$) are obtained.

$e_2$) Alternatively, the phosphinic acid esters VI ($R^2$=$R^3$) can be prepared by direct reaction of IV ($R^6$=$R^7$=halogen)

with 3 to 10 equivalents, preferably 4 to 6 equivalents of $R^2_2Cu(CN)Li_2$, $R_2Li$, $R_2MgX$, $R^2ZnX$, $R^2_2Zn$, $R^2_{4-n}TiR^{22}_n$ (n<4), $P[O—R^{23}]_3$, preferably $R^2_2Cu(CN)Li_2$, $R^2MgX$, $P[O—R^{23}]_3$, in a suitable solvent, preferably THF or ether, at a temperature from –120° to 150° C., preferably –100° to 0° C. or 20° to 80° C. $[P[O—R^{23}]_3]$. $R^2$ and $R^{22}$ have the abovementioned meanings.

$R^{23}$ is $(C_1–C_6)$-alkyl, $(C_6–C_{12})$-aryl, $(C_7–C_{13})$-arylalkyl, where aryl can be substituted one or more times by fluorine, chlorine, bromine, $NO_2$, CN, OH, COOH, $(C_1–C_6)$-alkyl, $(C_1–C_6)$-alkoxy, $C(O)—O—(C_1–C_6)$-alkyl, $C(O)—(C_1–C_6)$-alkyl, $O—C(O)—(C_1–C_6)$-alkyl.

After working up and purification, e.g. by concentration, crystallization, extraction, purification on silica gel, the compounds VI ($R^2=R^3$) are obtained.

$e_3$) Phosphinic acid esters VI in which $R^3$ is not $R^2$ and $R^2$ and $R^3$ are as defined in I, are prepared as described in $e_1$), but first only 0.3 to 2 equivalents, preferably 1 to 1.2 equivalents, of the carbon nucleophiles which are produced from CH-acidic compounds such as e.g. $VIIa^1$ and $VIIb^1$, $VIII^1$, $IX^1$, of the organometallic compounds $R^2_2Cu(CN)Li_2$, $R^2Li$, $R^2MgX$, $R^2ZnX$, $R^2_2Zn$ or $R^2_{4-n}TiR^{22}_n$ (n<4), preferably nucleophiles formed from $VII^1$, $VIII^1$, $IX^1$, $R^2_2Cu(CN)Li_2$, $R^2MgX$, and then 0.5 to 4 equivalents preferably 1 to 1.3 equivalents, of the carbon nucleophiles which are generated from CH-acidic compounds such as e.g. $VIIa^2$ and $VIIb^2$, $VIII^2$, $IX^2$, of the organometallic compounds $R^3_2Cu(CN)Li_2$, $R^3Li$, $R^3MgX$, $R^3ZnX$, $R^3_2Zn$ $R^3_{4-n}TiR^{22}_n$ (n<4), preferably nucleophiles formed from $VII^2$, $VIII^2$, $IX^2$, $R^3_2Cu(CN)Li_2$, $R^3MgX$, are employed (in the above text the superscript to the Roman numerals means that the respective radicals with the superscript 1 and 2 differ).

$e_4$) Alternatively, phosphinic acid esters VI in which $R^3$ is not $R^2$ and $R^2$ and $R^3$ are as defined in I can be prepared as described in $e_2$), but first only 2 to 5 equivalents, preferably 3 to 3.5 equivalents, of $R^2_2Cu(CN)Li_2$, $R^2Li$, $R^2MgX$, $R^2ZnX$, $R^2_2Zn$ or $R^2_{4-n}TiR^{22}_n$ (n<4), preferably $R^2_2Cu(CN)Li_2$, $R^2MgX$, and then 0.5 to 4 equivalents, preferably 1 to 1.3 equivalents, of the carbon nucleophiles which are generated from CH-acidic compounds such as e.g. VIIa and VIIb, VIII, IX, of the compounds $R^3_2Cu(CN)Li_2$, $R^3MgX$, $R^3ZnX$, $R^3_2Zn$ or $R^3_{4-n}TiR^{22}_n$ (n<4) preferably nucleophiles formed from VII, VIII, IX, $R^3_2Cu(CN)Li_2$, $R^3MgX$, are employed $e_5$) Phosphinic acid esters VI in which $R^3$ is not $R^2$, $R^3=P(O)[O—R^{23}]_2$ and $R^2$ is as defined above can be prepared as described in $e_2$), but first only 0.5 to 5 equivalents, preferably 1 to 1.2 equivalents, of $P[O—R^{23}]_3$ and then 1 to 5 equivalents, preferably 2 to 2.2 equivalents of the compounds $R^2_2Cu(CN)Li_2$, $R^2Li$, $R^2MgX$, $R^2ZnX$, $R^2_2Zn$ or $R^2_{4-n}TiR^{22}n$ (n<4) preferably $R^2_2Cu(CN)Li_2$, $R^2MgX$, are employed.

$e_6$) Phosphinic acid esters VI in which $R^3$ is not $R^2$, $R^3$ is $P(O)[O—R^{23}]_2$ and $R^2$ is $P(O)[O—R^{23'}]_2$ can be prepared as described in $e_2$), but first only 0.5 to 5 equivalents, preferably 1 to 1.2 equivalents, of $P[O—R^{23}]_3$ and then 0.5 to 5 equivalents, preferably 1 to 1.2 equivalents, of $P[O—R^{23'}]_3$ are employed.

$R^{23'}$ can have the same meanings as defined above for $R^{23}$, but in this actual case is not $R^{23}$.

$e_7$) Phosphinic acid esters VI in which $R^3$ is hydrogen and $R^2$ is as defined in formula I but is not hydrogen can be prepared from Vb ($R^7=H$) as described in $e_1$), but only 0.5 to 5 equivalents, preferably 1 to 1.2 equivalents, of the carbon nucleophiles which are generated from CH-acidic compounds such as e.g. VIIa and VIIb, VIII, of the organometallic compounds $R^2_2Cu(CN)Li_2$, $R^2Li$, $R^2MgX$, $R^2ZnX$, $R^2_2Zn$ or $R^2TiR^{22}_3$, $P[O—(C_1–C_6)$-alkyl$]_3$, preferably VII, VIII, $P[O—(C_1–C_6)$-alkyl$]_3$, $R^2_2Cu(CN)Li_2$, $R^2MgX$, are employed.

$e_8$) Alternatively, phosphinic acid esters VI in which $R^3$ is hydrogen and $R^2$ is as defined above but is not hydrogen can be prepared from IV ($R^7=H$) as described in $e_2$), but only 0.5 to 10 equivalents, preferably 2 to 3 equivalents, of the organometallic compounds $R^2_2Cu(CN)Li_2$, $R^2Li$, $R^2MgX$, $R^2ZnX$, $R^2_2Zn$ or $R^2TiR^{22}_3$, preferably $R^2_2Cu(CN)Li_2$, $R^2MgX$, are employed.

The starting compounds of the formula IV can be prepared in different ways, e.g. first, starting from a compound of the formula (II), the amino groups of the bis(aminomethyl)phosphinic acid can be protected [synthesis according to L. Meier, J. Organomet. Chem. 178 (1979) 157] (formula II)

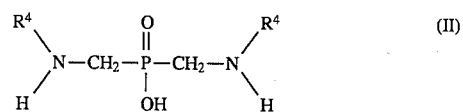

In formula II, $NHR^4$ is intended to be the protected amino function. The generally known protective groups for amino functions [Greene, Protective Groups in Organic Synthesis, Wiley 1979] can be employed in a manner known per se, but in particular the protective groups known for peptide chemistry [Bodanszky & Bodanszky, The Practice of Peptide Synthesis, Springer 1984] are introduced in the manner generally known for amino acids. Preferred protective groups are carbamates and acyl protective groups. The tert-butoxycarbonyl (Boc), 9-fluorenylmethoxycarbonyl (Fmoc), 2,2,2-trichloroethoxycarbonyl, acetyl and benzoyl protective groups are particularly preferred. The Boc and the benzoyl protective group are very particularly preferred.

For example, the bis(aminomethyl)phosphinic acid is reacted with 1 to 5 equivalents, preferably 2 to 2.5 equivalents, of acyl chloride, acyl anhydride or acyl active ester, preferably acyl chloride, in the presence of a base, preferably pyridine, at –30° to +80° C., preferably at –10° to +20° C., for 2 to 3 hours. Working up is carried out by concentration, acidification and extraction.

A further example is the reaction of bis(aminomethyl)phosphinic acid with 1 to 5 equivalents, preferably 2 to 2.5 equivalents, of di-tert-butyl pyrocarbonate in the presence of a small excess of base (relative to the amino groups), preferably NaOH in aqueous dioxane, at –30° to +50° C., preferably at –10° to +20° C., for 2 to 3 hours. Working up is carried out, as described in Bodanszky for amino acids, in a manner known per se by concentration, acidification to pH 2–3 and extraction.

The N,N'-protected bis(aminomethyl)phosphinic acid II can be esterified in the next step with $R^5$—OH to give III, $R^5OH$ having the abovementioned meanings.

$R^4$ and $R^5$ preferably have the abovementioned meanings.

Esterification is carried out by reaction of the protected phosphinic acid II, the compound $R^5$—OH (where $R^5$ is as defined above) and a suitable coupling reagent. The conditions for the esterification depend on the generally known procedures for the esterification of phosphonic acids, as are mentioned e.g. in Houben-Weyl (Volume 12/1 & E2). Alternatively, coupling reagents such as are employed for the esterification of N-protected α-amino carboxylic acids [Janin et al., Tetrahedron Lett. 28 (1987) 1661] can be used or coupling reagents which are used in DNA synthesis for the synthesis of phosphoric acid triesters [Sonveaux, Bioorg. Chem. 14 (1986) 274] can also be employed.

The reaction of II with 0.5–10 equivalents, preferably 1 to 5 equivalents, of $R^5$—OH and 0.5 to 2 equivalents, preferably 1–1.2 equivalents, of dicyclohexylcarbodiimide (DCC) in a suitable organic solvent, preferably THF, at temperatures of 0°–100° C., preferably at 40°–70° C. (in THF at 40°–67° C.) for 0.5 to 48 hours is particularly preferred. The esters III obtained are purified in a manner known per se by concentration, removal of N,N'-dicyclohexylurea by filtration, crystallization or chromatography on silica gel.

The reaction of II with alkyl chloroformates or alkenyl chloroformates which are employed for the esterification of α-aminocarboxylic acids [Janin et al., Tetrahedron Lett. 28 (1987) 1661] is also particularly preferred. To this end, II is reacted with 0.5 to 3 equivalents, preferably 1 to 1.3 equivalents, of alkyl or alkenyl chloroformate, preferably isobutyl or isopropenyl chloroformate, in the presence of 0.5 to 3, preferably 1 to 1.2 equivalents, of trialkylamine, particularly preferably triethylamine (TEA) or diisopropylethylamine (DIPEA), and a catalytic amount of dimethylaminopyridine (DMAP), preferably 0.1 equivalents of DMAP, and also 0.5 to 10 equivalents, preferably 1 to 5 equivalents, of $R^5$—OH in a suitable organic solvent, preferably methylene chloride ($CH_2Cl_2$), chloroform ($CHCl_3$), tetrahydrofuran (THF), acetonitrile, dimethylformamide (DMF), dimethyl sulfoxide (DMSO), dioxane, toluene, benzene, ethyl acetate (EA), particularly preferably $CH_2Cl_2$ or $CHCl_3$ and toluene, at temperatures from –10° to +50° C., preferably 0°–10° C., for 1 to 12 hours. Working up and purification is carried out in a manner known per se, such as described in the esterification of α-amino acids [Janin et al., Tetrahedron Lett. 28 (1987) 1661] by extraction, crystallization, chromatography on silica gel.

The N,N-protected bis(aminomethyl)phosphinic acid derivatives III can be converted in the next step to compounds of the formula IV

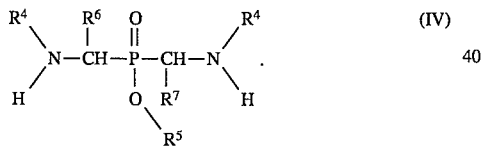

$R^4$, $R^5$, $R^6$ and $R^7$ preferably have the abovementioned meanings.

$R^6$ and $R^7$ are introduced e.g. by the reaction of III with 0.5 to 10 equivalents, preferably 1 to 5 equivalents, of halogen, preferably bromine, in a suitable organic solvent, preferably tetrachloromethane, at a temperature from –20° to 115° C. with irradiation in the presence of free-radical initiators such as peroxides, azo compounds or UV light, preferably suitable peroxides or azo compounds, particularly preferably at a temperature from 60° to 90° C. in the presence of azobis(isobutyronitrile), in the course of 5 minutes to 24 hours, preferably 45 minutes to 6 hours, preferably under a protective gas atmosphere. Working up and purification of the compounds IV are carried out by generally customary processes such as filtration, concentration, crystallization, chromatography.

The introduction of $R^6$ and $R^7$ can also be carried out by the reaction of III with 0.5 to 10 equivalents, preferably 1 to 5 equivalents, of N-bromoamide such as N-bromosuccinimide (NBS), N-bromohydantoin, N-bromocaprolactam, N-chlorosuccinimide, N-chloro-N-cyclohexylbenzenesulfonamide or tert-butyl hypochlorite, preferably N-bromosuccinimide, in a suitable organic solvent, preferably tetrachloromethane, at a temperature from –20° to 115° C., preferably 5° to 80° C., with irradiation and/or in the presence of suitable free-radical initiators in the course of 5 minutes to 100 hours, preferably 1 to 40 hours, preferably under a protective gas atmosphere. Working up and purification of the compounds IV is carried out by generally customary processes such as filtration, concentration, crystallization, chromatography.

Monosubstituted compounds IV ($R^7$=H) are formed when 1 to 1.2 equivalents of halogen or the abovementioned N-halo compounds are used according to the methods described above.

The invention furthermore relates to the compounds of the formula VI

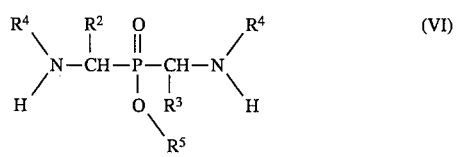

in which $R^2$ and $R^3$, independently of one another, are $P(O)[OH]_2$, $P(O)(OR^{23})_2$, where $R^{23}$ independently of one another is ($C_1$–$C_6$)-alkyl, ($C_6$–$C_{12}$)-aryl or ($C_7$–$C_{13}$)-arylalkyl, where aryl can be substituted one or more times by fluorine, chlorine, bromine, $NO_2$, CN, OH, COOH, ($C_1$–$C_6$)-alkyl, ($C_1$–$C_6$)-alkoxy, C(O)—O—($C_1$–$C_6$)-alkyl, C(O)—O—($C_6$–$C_{12}$)-aryl, C(O)—($C_1$–$C_6$)-alkyl, C(O)—($C_6$–$C_{12}$)-aryl, O—C(O)—($C_1$–$C_6$)-alkyl or O—C(O)—($C_6$–$C_{12}$)-aryl, $R^4$ is a protective group for the amino function and $R^5$ is ($C_1$–$C_{18}$)-alkyl, ($C_2$–$C_{18}$)-alkenyl, ($C_2$–$C_{18}$)-alkynyl, ($C_6$–$C_{12}$)-aryl, ($C_7$–$C_{20}$)-arylalkyl, where alkyl, alkenyl, alkynyl and aryl can be substituted one or more times by fluorine, chlorine, bromine, oxo, $NO_2$, $NH_2$ or protected form, CN, OH, COOH, ($C_1$–$C_6$)-alkyl, ($C_1$–$C_6$)-alkoxy, C(O)—O—($C_1$–$C_6$)-alkyl, C(O)—O—($C_6$–$C_{12}$)-aryl, C(O)—($C_1$–$C_6$)-alkyl, C(O)—($C_6$–$C_{12}$)-aryl, O—C(O)—($C_1$–$C_6$)-alkyl or O—C(O)—($C_6$–$C_{12}$)-aryl.

Particularly preferred compounds of the formula VI are those in which $R^2$ and $R^3$ independently of one another are $P(O)[OH]_2$, $P(O)[O—(C_1$–$C_4)$-alkyl$]_2$, $P(O) [O—(C_6$–$C_{12})$-aryl$]_2$ or $P(O)[O—(C_7$–$C_{13})$-arylalkyl$]_2$ and $R^5$ is ($C_1$–$C_6$)-alkyl, ($C_6$–$C_{12}$)-aryl or ($C_7$–$C_{13}$)-arylalkyl, where aryl can be substituted by Cl, Br or ($C_1$–$C_3$)-alkyl.

The invention furthermore relates to the compounds of the formula I

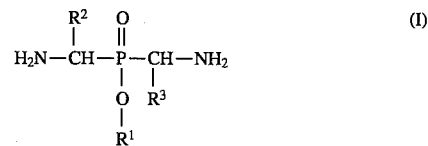

wherein $R^1$ is H, ($C_1$–$C_{18}$)-alkyl, ($C_2$–$C_{18}$)-alkenyl, ($C_2$–$C_{18}$)-alkynyl, ($C_6$–$C_{12}$)-aryl, ($C_7$–$C_{20}$)-arylalkyl, where alkyl, alkenyl, alkynyl and aryl can be substituted one or more times by fluorine, chlorine, bromine, oxo, $NO_2$, $NH_2$ or protected form, CN, OH, COOH, ($C_1$–$C_6$)-alkyl, ($C_1$–$C_6$)-alkoxy, C(O)—O—($C_1$–$C_6$)-alkyl, C(O)—O—($C_6$–$C_{12}$)-aryl, C(O)—($C_1$–$C_6$)-alkyl, C(O)—($C_6$–$C_{12}$)-aryl, O—C(O)—($C_1$–$C_6$)-alkyl, O—C(O)—($C_6$–$C_{12}$)-aryl, and $R^2$ and $R^3$ independently of one another are $P(O) [OH]_2$, $P(O)(OR^{23})_2$, where $R^{23}$ independently of one another is ($C_1$–$C_6$)-alkyl, ($C_6$–$C_{12}$)-aryl or ($C_7$–$C_{13}$)-arylalkyl, where aryl can be substituted one or more times by fluorine, chlorine, bromine, $NO_2$, CN, OH, COOH, $(C_1-C_6)$-alkyl, $(C_1-C_6)$-alkoxy, C(O)—O—$(C_1-C_6)$-alkyl, C(O)—O—$(C_6-C_{12})$-aryl, C(O)—$(C_1-C_6)$-alkyl, C(O)—$(C_6-C_{12})$-aryl, O—C(O)—$(C_1-C_6)$-alkyl or O—C(O)—$(C_6-C_{12})$-aryl.

Particularly preferred compounds of the formula I are those in which $R^1$ is H, $(C_1-C_6)$-alkyl, $(C_6-C_{12})$-aryl, $(C_7-C_{13})$-arylalkyl, where aryl can be substituted by Cl, Br or $(C_1-C_3)$-alkyl, and $R^2$ and $R^3$ independently of one another are P(O)[OH]$_2$, P(O)[O—$(C_1-C_4)$-alkyl]$_2$, P(O)[O—$(C_6-C_{12})$-aryl]$_2$ or P(O)[O—$(C_7-C_{13})$arylalkyl]$_2$.

The present invention furthermore includes the acidic salt forms of the α- or α,α'-substituted derivatives of the compounds of the formulae I and VI of bis(aminomethyl)phosphinic acid, in particular hydrogen chlorides, hydrogen bromides, hydrogen sulfates, acetates, particularly preferably hydrogen chlorides and hydrogen bromides.

The compounds of the formulae VI and I according to the invention are active as enzyme inhibitors and are intermediates in the synthesis of pharmaceutical substances and plant protection agents.

$f_1$) For the synthesis of the compounds of the formula I in which $R^1$ and $R^5$ are identical, the protective groups $R^4$ are removed by the customary processes [Greene, Protective Groups in Organic Synthesis, Wiley 1979].

Thus, e.g. for $R^4$=Boc, the protective group in VI is removed with HCl or HBr in a suitable organic solvent, preferably ether, methanol, dioxane, diethoxyethane, at a temperature from 0° to 50° C., preferably 10° to 30° C., for 1 to 48 hours, preferably 1 to 5 hours. For working up and purification of the compound I, generally known methods are used, such as filtration, extraction, recrystallization, lyophilization and chromatography. Customarily the residue is taken up in water after concentration. The aqueous phase is then stirred with solid $K_2CO_3$ and $CH_2Cl_2$ and I is obtained from the organic phase. For purification, it can additionally be chromatographed on silica gel. I can be converted into the corresponding salts by ion exchange chromatography or by reaction with acids.

$f_2$) For the synthesis of the compounds of the formula I in which $R^1$ is not $R^5$, the compounds VI are stirred in aqueous HBr, HCl, HBr in glacial acetic acid, preferably in aqueous HCl. The reaction is carried out at 0°–120° C., preferably at 70°–100° C. The reaction time is 1 to 72 hours, preferably 1 to 24 hours. For working up and purification, generally known methods are used, such as filtration, extraction, recrystallization, lyophilization and chromatography. I can be converted into corresponding salts by ion exchange chromatography or by reaction with acids.

$f_3$) Compounds of the formula I in which $R^1$ is not $R^5$ can alternatively be obtained from compounds of the formula I in which $R^1$ is $R^5$. The preparation methods depend on the specific properties of the radical $R^1$ to be removed (which is $R^5$), by generally known processes. By way of example, the removal of $R^5$=benzyl by hydrogenation or of $R^5$=methyl or ethyl by reaction with trimethylsilyl bromide or trimethylsilyl iodide in a suitable organic solvent such as, for example, dioxane at room temperature may be mentioned.

The present invention is illustrated in greater detail by the following exemplary embodiments and by the contents of the patent claims.

EXAMPLES

Example 1

Bis(N-tert-butoxycarbonylaminomethyl)phosphinic acid (1)

1.0M aqueous sodium hydroxide solution (37.6 ml; 37.60 mmol) and tert-butoxycarbonyl anhydride (5.69 g; 26.10 mmol) in dioxane (3 ml) are added successively with stirring at 0° C. to a solution of bis(aminomethyl)phosphinic acid hydrochloride (2.00 g; 12.46 mmol) in water (20 ml) and dioxane (20 ml). The reaction solution is warmed to room temperature and concentrated to a volume of about 40 ml after an hour under reduced pressure. The solution is mixed with ethyl acetate (40 ml) and acidified with saturated aqueous $KHSO_4$ solution to a pH of 2–3. The separated aqueous phase is extracted with ethyl acetate (4×50 ml). The combined organic phase is dried over $Na_2SO_4$ and concentrated under reduced pressure. The phosphinic acid 1 (3.20 g) is obtained as a crude product.

$^1$H-NMR (δ/ppm/)(200 MHz, $CDCl_3$): 1.48 (18H, s, $(CH_3)_3C$); 3.53 (4H, bd, J 7.5 Hz, $PCH_2$); 5.70 (1H, bs, NH); 6.25 (1H, bs, NH);

MS (FAB, NBA, m/e): 325 (M+H$^+$), 269 (M-55), 213 (269-56) (100%).

Example 2

Bis(N-benzoylaminomethyl)phosphinic acid (2)

Benzoyl chloride (1.8 ml; 15.49 mmol) is added slowly with stirring at 0° C. to a solution of bis(aminomethyl)phosphinic acid hydrochloride (1.20 g; 7.48 mmol) in pyridine (8 ml). The reaction mixture is concentrated under reduced pressure. The residue is taken up in 5% hydrochloric acid (60 ml). The aqueous phase is extracted with ethyl acetate (3×60 ml). The combined organic phases are dried (sodium sulfate) and concentrated under reduced pressure. The phosphinic acid 2 (1.95 g) is obtained as a crude product.

$^1$H-NMR (δ/ppm/)(200 MHz, DMSO-$d_6$): 3.55 (4H, bd, J 7.5 Hz, $PCH_2$); 7.20–8.10 (10H, m, $H_{arom.}$);

MS (FAB, NBA, m/e): 333 (M+H$^+$)(100%).

Example 3

Ethyl bis(N-tert-butoxycarbonylaminomethyl)phosphinate (3)

DCC (190 mg, 0.92 mmol) in THF (4 ml) is added dropwise in the course of 4 minutes to a solution of the phosphinic acid 1 (270 mg, 0.83 mmol) in dry THF (4 ml) and abs. ethanol (0.30 ml, 5.15 mmol) which is boiling under reflux. After 1.5 hours (checking by TLC), the reaction solution is cooled to room temperature and filtered. The filter residue is washed with ether. The filtrate is extracted with water (2×20 ml). The organic phase is dried over $Na_2SO_4$ and concentrated under reduced pressure. After purification by column chromatography on silica gel (ethyl acetate/ heptane=3:2), the phosphinic acid ester 3 (100 mg, 34% of theory) is obtained. M.p. 117.5°–120° C.

$^1$H-NMR (δ/ppm/)(200 MHz, $CDCl_3$): 1.30 (3H, t, J 7 Hz, $CH_2CH_3$); 1.45 (18H, s, $(CH_3)_3C$); 3.23 (2H, dt, J 15 and 5 Hz, $PCH_2$); 3.84 (2H, m, $PCH_2$); 4.18 (2H, dq, J 6 and 6 Hz, $OCH_2$); 5.48 (2H, bs, NH);

MS (FAB, NBA, m/e): 353 (M+H$^+$); 297; 241 (100%).

Example 4

Ethyl bis(N-tert-butoxycarbonylaminomethyl)phosphinate (3)

Isobutyl chloroformate (1.50 ml, 11.48 mmol) is added dropwise with stirring at 0° C. to a solution of the phosphinic acid 1 (3.200 g, 9.88 mmol) in a mixture of methylene chloride (50 ml), ethanol (3.00 ml, 51.59 mmol), triethylamine (1.40 ml, 10.06 mmol) and N,N-dimethylpyridine (10 mg). After 90 minutes, the reaction solution is extracted with saturated aqueous ammonium chloride solution (30 ml) and saturated aqueous $KHCO_3$ solution (30 ml). The organic phase is dried over $Na_2SO_4$ and concentrated under reduced pressure. After purification by column chromatography on silica gel (ethyl acetate/heptane=3:2), the phosphinic acid ester 3 (1.840 g, 53% of theory) is obtained. See above spectroscopic data.

Example 5

Ethyl bis(N-benzoylaminomethyl)phosphinate (4)

In analogy to Example 4, 47% of the ethyl phosphinate 4 was prepared from the phosphinic acid 2 in a yield of 47%.

$^1$H-NMR ($\delta$/ppm/)(200 MHz, DMSO-$d_6$): 1.31 (3H, t, J 7 Hz, $CH_2CH_3$); 3.25 (2H, dr, J 15 and 5 Hz, $PCH_2$); 3.87 (2H, m, $PCH_2$); 4.19 (2H, dq, J 6 and 6 Hz, $OCH_2$); 7.18–8.10 (10H, m, $H_{arom.}$);

MS (FAB, NBA, m/e): 361 (M+H$^+$)(100%).

Example 6

Benzyl bis(N-tert-butoxycarbonylaminomethyl)phosphinate (5)

In analogy to Example 4, the benzyl phosphinate 5 was prepared from the phosphinic acid 1 and benzyl alcohol in a yield of 55%.

$^1$H-NMR ($\delta$/ppm/)(200 MHz, DMSO-$d_6$): 1.44 (18H, s, $(CH_3)_3C$); 3.28 (2H, dr, J 15 and 5 Hz, $PCH_2$); 3.88 (2H, m, $PCH_2$); 5.13 (2H, d, J 6 Hz, $CH_2Ph$); 5.25 (2H, m, NH); 7.15–7.45 (10H, m, $H_{arom.}$);

MS (FAB, NBA, m/e): 415 (M+H$^+$)(100%).

Example 7

Ethyl bis(N-tert-butoxycarbonylamino(bromo)methyl)phosphinate (6)

The Boc-protected phosphinic acid ester 3 (120 mg, 0.34 mmol) and N-bromosuccinimide (121 mg, 0.68 mmol) are illuminated with a 300 watt incandescent lamp with cooling (20° C.) for 2 hours in carbon tetrachloride (15 ml). The succinimide deposited is filtered off with suction. After concentration under reduced pressure, the bromophosphinic acid ester 6 (167 mg, 96% of theory) is obtained.

$^1$H-NMR ($\delta$/ppm/)(200 MHz, CDCl$_3$): 1.30 (3H, t, J 7 Hz, $CH_2CH_3$); 1.45 (18H, s, $(CH_3)_3C$); 4.18 (2H, dq, J 6 and 6 Hz, $OCH_2$); 6.45 (2H, m, PCH).

Example 8

Ethyl bis(N-benzoylamino(bromo)methyl)phosphinate (7)

In analogy to Example 7, the bromophosphinic acid ester 7 is obtained from the N-benzoyl-protected phosphinic acid ester 4 and reacted further as a crude product.

$^1$H-NMR ($\delta$/ppm/)(200 MHz, CDCl$_3$): 1.28 (3H, t, J 7 Hz, $CH_2CH_3$); 4.20 (2H, m, $OCH_2$); 6.45 (2H, m, PCH); 7.20–7.80 (12 H, m, $H_{arom.}$+2×NH).

Example 9

Benzyl bis(N-tert-butoxycarbonylamino(bromo)methyl)phosphinate (8)

In analogy to Example 7, the bromophosphinic acid ester 8 is obtained from the N-Boc-protected benzyl phosphinate 5 and reacted further as a crude product.

$^1$H-NMR ($\delta$/ppm/)(200 MHz, CDCl$_3$): 1.44 (18H, s, $(CH_3)_3C$); 5.15 (2H, m, $CH_2Ph$); 6.45 (2H, m, PCH); 7.12–7.50 (5H, m, $H_{arom.}$).

Example 10

Benzyl N-tert-butoxycarbonylamino(bromo)methyl, N-tert-butoxycarbonylaminomethylphosphinate (9)

In analogy to Example 7, the monosubstituted bromophosphinic acid ester 9 is obtained from the N-Boc-protected benzyl phosphinate 5 using only one equivalent of N-bromosuccinimide and reacted further as a crude product.

$^1$H-NMR ($\delta$/ppm/)(200 MHz, CDCl$_3$): 1.44 (18H, s, $(CH_3)_3C$); 3.85 (2H, m, $PCH_2$) 5.13 (2H, m, $CH_2Ph$); 6.44 (1H, m, PCH); 7.12–7.50 (5H, m, $H_{arom.}$).

Example 11

Ethyl bis(N-tert-butoxycarbonyl-1-amino-2-phenylethyl)phosphinate (10)

A 2.00N benzylmagnesium chloride solution (1.35 ml; 2.70 mmol) in THF is added dropwise to a solution of the bromide 6 (340 mg; 0.67 mmol) in THF (10 ml), which is stirred at −78° C. under an argon atmosphere. After stirring at −70° C. for 3 hours, the reaction solution is warmed to room temperature and mixed with saturated aqueous ammonium chloride solution (50 ml). The aqueous phase is extracted with ethyl acetate (3×60 ml). The combined organic phase is dried over $Na_2SO_4$ and concentrated under reduced pressure. After purification by column chromatography on silica gel (ethyl acetate/heptane), the bisalkylated phosphinic acid ester 10 (105 mg, 30% of theory) is obtained.

$^1$H-NMR ($\delta$/ppm/)(200 MHz, CDCl$_3$): 1.35 (3H, t, J 7 Hz, $CH_2CH_3$); 1.45 (18H, s, $(CH_3)_3C$); 3.05 (2H, m, $CH_2Ph$); 3.45 (2H, m, $CH_2Ph$); 4.15–4.30 (4H, m, $OCH_2$+2×CH—$CH_2Ph$); 6.90–8.00 (10H, m, $H_{arom.}$);

MS (FAB, NBA, m/e): 532 (M+H$^+$)(100%).

Example 12

Ethyl bis(N-benzoylamino(2-cyclohexanone)methyl)-phosphinate (11)

N-Ethyldiisopropylamine (140 μl; 0.82 mmol) is added dropwise to a solution of the bromide 7 (210 mg; 0.41 mmol) in absolute THF, which is stirred at −78° C. under an argon atmosphere. After 2 hours, 1-morpholino-1-cyclohexene (138 μl; 0.82 mmol) in THF (10 ml) is added dropwise to the reaction solution. The mixture is warmed to room temperature in the course of 8 hours and hydrolyzed with 10% aqueous citric acid (30 ml). After neutralization with saturated, aqueous $NaHCO_3$ solution, extraction with ethyl acetate, drying over $Na_2SO_4$, concentration under reduced pressure and purification by column chromatography, a mixture of the diastereomeric phosphinic acid esters 11 (79 mg, 35% of theory) is obtained.

$^1$H-NMR (δ/ppm/)(200 MHz, CDCl$_3$): 1.30 (3H, m, CH$_3$/diastereomer mixture); 1.45–2.37 (16H, m, —(CH$_2$)$_4$—); 3.18 (2H, m, CHCO); 4.20 (2H, m, OCH$_2$); 4.72 (2H, m, PCH) 7.20–7.80 (12H, m, H$_{arom.}$+2NPH);

MS (FAB, NBA, m/e): 553 (M+H$^+$)(100%).

Example 13

Benzyl bis(N-tert-butoxycarbonylamino(phenyl)methyl)phosphinate (12)

In analogy to Example 11, the benzyl phosphinate 12 is prepared from the bis-substituted benzyl bromophosphinate 8 and a 2.0N phenylmagnesium chloride solution in a yield of 32%.

MS (FAB, NBA, m/e): 567 (M+H$^+$)(100%).

Example 14

Benzyl N-tert-butoxycarbonylaminomethyl, N-tert-butoxycarbonylamino(phenyl)methylphosphinate (13)

In analogy to Example 11, the benzyl phosphinate 13 is prepared from the mono-substituted benzyl bromophosphinate 9 and a 2.0N phenylmagnesium chloride solution in a yield of 29%.

MS (FAB, NBA, m/e): 491 (M+H$^+$)(100%).

Example 15

Ethyl bis(N-benzoylamino(diethoxyphosphoryl)methyl)phosphinate (14)

A solution of the bromide 7 (195 mg; 0.38 mmol) and triethyl phosphite (130 µl; 0.76 mmol) in abs. THF (50 ml) is concentrated under reduced pressure after stirring at room temperature for 4 hours. A mixture of the diastereomeric phosphinic acid esters 14 (145 mg, 64% of theory after recrystallization from ethyl acetate) is obtained.

$^1$H-NMR (δ/ppm/)(200 MHz, CDCl$_3$): 1.30 (15H, m, CH$_3$); 4.18 (10H, m, OCH$_2$); 5.15 (2H, m, PCH); 7.10–7.80 (12H, m, H$_{arom.}$+2NH);

MS (FAB, NBA, m/e): 601 (M+H$^+$)(100%).

Example 16

Ethyl bis(1-amino-2-phenylethyl)phosphinate hydrochloride (15)

An about 3N methanolic hydrochloric acid (10 ml) is added at room temperature with stirring to a solution of the bisalkylated phosphinic acid ester 10 (103 mg, 0.19 mol) in methanol (5 ml). After 3 hours, the reaction solution is concentrated under reduced pressure. The phosphinic acid ester hydrochloride 15 (69 mg, 97% of theory) is obtained.

$^1$H-NMR (δ/ppm/)(200 MHz, DMSO-d$_6$): 1.15 (3H, m, CH$_3$); 3.05 (4H, m, CH$_2$Ph); 3.93 (1H, m, CH); 4.14–4.45 (3H, m, CH+OCH$_2$); 7.20–7.45 (10H, m, H$_{arom.}$); 8.70 (6H, bs, NH$_3^⊕$);

MS (FAB, NBA, m/e): 333 (M+H$^+$); 214; 120 (100%).

Example 17

Bis(1-amino-2-phenylethyl)phosphinic acid hydrochloride (16)

A solution of the bisalkylated phosphinic acid ester 10 (170 mg, 0.32 mmol) in 37% aqueous hydrochloric acid (20 ml) is heated to a temperature of about 100° C. for 6 hours. After concentration of the reaction solution under reduced pressure and repeated coevaporation with methanol and toluene, the phosphinic acid hydrochloride 16 (101 mg, 93% of theory) is obtained.

$^1$H-NMR (δ/ppm/)(200 MHz, DMSO-d$_6$): 3.03 (4H, m, CH$_2$Ph); 3.95 (1H, m, CH): 4.21 (1H, m, CH); 7.20–7.45 (10H, m, H$_{arom.}$); 8.72 (6H, bs, NH$_3^⊕$);

MS (FAB, NBA, m/e): 305 (M+H$^+$); 120 (100%).

What is claimed is:

1. A process for the preparation of compounds of the formula VI

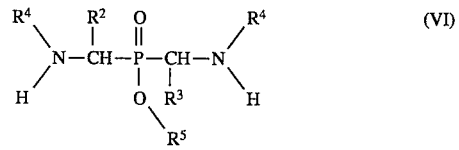

in which R$^2$ and R$^3$, independently of one another, are hydrogen, (C$_1$–C$_{18}$)-alkyl, (C$_2$–C$_{18}$)-alkenyl, (C$_2$–C$_{18}$)-alkynyl, where alkyl, alkenyl and alkynyl are unsubstituted or substituted one or more times by fluorine, chlorine, bromine, COOH, oxo, NO$_2$, NH$_2$, NHC(O)—(C$_1$–C$_6$)-alkyl, NHC(O)—(C$_6$–C$_{12}$)-aryl, CN, OH, CHO, CH-[(C$_1$–C$_6$)-alkoxy]$_2$, SO$_3$H, C(O)—O—(C$_1$–C$_6$)-alkyl, C(O)—O—(C$_6$–C$_{12}$)-aryl, C(O)—(C$_1$–C$_6$)-alkyl, C(O)—(C$_6$–C$_{12}$)-aryl, O—C(O)—(C$_1$–C$_6$)-alkyl, O—C(O)—(C$_6$–C$_{12}$)-aryl, (C$_1$–C$_6$)-alkoxy; are (C$_6$–C$_{12}$)-aryl, (C$_7$–C$_{22}$)-arylalkyl, where aryl is unsubstituted or substituted one or more times by fluorine, chlorine, bromine, NO$_2$, NH$_2$, NHC(O)—(C$_1$–C$_6$)-alkyl, NHC(O)—(C$_6$–C$_{12}$)-aryl, CN, OH, COOH, (C$_1$–C$_6$)-alkyl, (C$_1$–C$_6$)-alkoxy, C(O)—O—(C$_1$–C$_6$)-alkyl, C(O)—O—(C$_6$–C$_{12}$)-aryl, C(O)—(C$_1$–C$_6$)-alkyl, C(O)—(C$_6$–C$_{12}$)-aryl, O—C(O)—(C$_1$–C$_6$)-alkyl, O—C(O)—(C$_6$–C$_{12}$)-aryl; or are P(O)[OH]$_2$, P(O)(OR$^{23}$)$_2$, where R$^{23}$ independently of one another is (C$_1$–C$_6$)-alkyl, (C$_6$–C$_{12}$)-aryl or (C$_7$–C$_{13}$)-arylalkyl and where aryl is unsubstituted or substituted one or more times by fluorine, chlorine, bromine, NO$_2$, CN, OH, COOH, (C$_1$–C$_6$)-alkyl, (C$_1$–C$_6$)-alkoxy, C(O)—O—(C$_1$–C$_6$)-alkyl, C(O)—O—(C$_6$–C$_{12}$)-aryl, C(O)—(C$_1$–C$_6$)-alkyl, C(O)—(C$_6$–C$_{12}$)-aryl, O—C(O)—(C$_1$–C$_6$)-alkyl or O—C(O)—(C$_6$–C$_{12}$)-aryl, where R$^2$ and R$^3$ are not simultaneously hydrogen;

R$^4$ is a protective group for the amino function and

R$^5$ is (C$_1$–C$_{18}$)-alkyl, (C$_2$–C$_{18}$)-alkenyl, (C$_2$–C$_{18}$)-alkynyl, (C$_6$–C$_{12}$)-aryl, (C$_7$–C$_{20}$)-arylalkyl, where alkyl, alkenyl, alkynyl and aryl are unsubstituted or substituted one or more times by fluorine, chlorine, bromine, oxo, NO$_2$, NH$_2$ or protected form, CN, OH, COOH, (C$_1$–C$_6$)-alkyl, (C$_1$–C$_6$)-alkoxy, C(O)—O—(C$_1$–C$_6$)-alkyl, C(O)—O—(C$_6$–C$_{12}$)-aryl, C(O)—(C$_1$–C$_6$)-alkyl, C(O)—(C$_6$–C$_{12}$)-aryl, O—C(O)—(C$_1$–C$_6$)-alkyl, O—C(O)—(C$_6$–C$_{12}$)-aryl, which comprises converting a compound of the formula IV

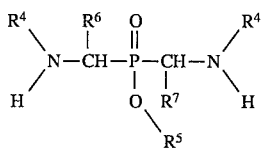

(IV)

in which $R^4$ and $R^5$ have the abovementioned meaning and $R^6$ and $R^7$ independently of one another are H, Cl or Br, where not both radicals are simultaneously hydrogen a) by reaction with a base to a compound of the formula Va or Vb

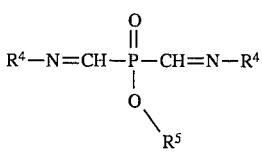

(Va)

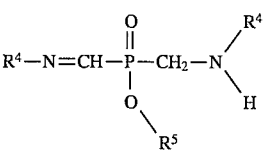

(Vb)

where $R^4$ and $R^5$ have the abovementioned meanings and for the preparation of the compound VI, a compound of the formula Va or Vb is reacted with carbon nucleophiles; or b) the compound of the formula VI is prepared by direct reaction of a compound of the formula IV with $R^2_2Cu(CN)Li_2$, $R^2Li$, $R^2MgX$, $R^2ZnX$, $R^2_2Zn$, $R^2_{4-n}TiR^{22}_n$ (n<4), $P[O—R^{23}]_3$, where $R^2$ has the abovementioned meaning; $R^{22}$ is $N—[(C_1-C_6)$-alkyl$]_2$, $O—(C_1-C_6)$-alkyl, $O—(C_6-C_{12})$-aryl, where aryl is unsubstituted or substituted by fluorine, chlorine, bromine, $NO_2$, $NH_2$ or protected form, CN, OH, COOH, $C(O)—O—(C_1-C_6)$-alkyl, $(C_1-C_6)$-alkyl, $(C_1-C_6)$-alkoxy, or is a tartaric acid derivative; and, $R^{23}$ is $(C_1-C_6)$-alkyl $(C_6-C_{12})$-aryl, $(C_7-C_{13})$-arylalkyl, where aryl is unsubstituted or substituted one or more times by fluorine, chlorine, bromine, $NO_2$, CN, OH, COOH, $(C_1-C_6)$-alkyl, $(C_1-C_6)$-alkoxy, $C(O)—O—(C_1-C_6)$-alkyl, $C(O)—(C_1-C_6)$-alkyl, $O—C(O)—(C_1-C_6)$-alkyl, and X is a leaving group.

2. The process as claimed in claim 1, wherein $R^2$ and $R^3$ independently of one another are $(C_1-C_6)$-alkyl, $(C_2-C_6)$-alkenyl, $(C_2-C_6)$-alkynyl, where alkyl is unsubstituted or substituted one or more times by oxo, fluorine, chlorine, bromine, COOH, $C(O)—(C_1-C_6)$-alkyl, $C(O)—O—(C_1-C_6)$-alkyl, $(C_6-C_{12})$-aryl, $(C_7-C_{13})$-arylalkyl, where aryl is unsubstituted or substituted one or more times by chlorine, bromine, CN, $(C_1-C_3)$-alkoxy; $P(O)[OH]_2$, $P(O)(OR^{23})_2$, where $R^{23}$ is $(C_1-C_6)$-alkyl, $(C_6-C_{12})$-aryl or $(C_7-C_{13})$-arylalkyl, and $R^5$ is $(C_1-C_4)$-alkyl, $(C_2-C_4)$-alkenyl, phenyl, benzyl.

3. The process of claim 2, wherein $R^2$ and $R^3$ are $(C_1-C_6)$-alkyl, $(C_2-C_6)$-alkenyl, $(C_2-C_6)$-alkynyl, benzyl, $P(O)[OH]_2$ or $P(O)[O—(C_1-C_6)$-alkyl$]_2$, and $R^5$ is $(C_1-C_4)$-alkyl or benzyl.

4. The process as claimed in claim 2, wherein the base in the reaction of a compound of the formula IV is a tri-$(C_1-C_6)$-alkylamine, pyridine, butyllithium, lithium diisopropylamide (LDA), sodium hydride, sodium amide, potassium tert-butoxide, sodium amide-$R^{21}$ONa, $R^{21}$ being $(C_2-C_6)$-alkyl or $CH_3CH_2—O—CH_2CH_2$, or uncharged, peralkylated polyaminophosphazene bases.

5. The process of claim 4, wherein $R^{21}$ is a tri-$(C_1-C_3)$-alkylamine or pyridine.

6. The process as claimed in claim 1, wherein the carbon nucleophiles are selected from CH-acidic compounds of the formula VIIa, VIIb, VIII and IX

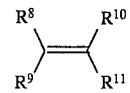

VII

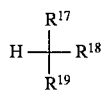

VIII

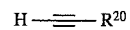

IX

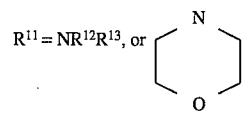

a

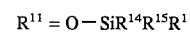

b $R^8$, $R^9$, $R^{10}$, identically or independently of one another, are hydrogen, $(C_1-C_{18})$-alkyl, $(C_2-C_{18})$-alkenyl, $(C_2-C_{18})$-alkynyl, $(C_6-C_{12})$-aryl, $(C_7-C_{20})$-arylalkyl, wherein alkyl, alkenyl, alkynyl and aryl are unsubstituted or substituted one or more times by fluorine, chlorine, bromine, $NO_2$, $NH_2$ or protected form, $(C_1-C_6)$-alkyl, $(C_1-C_6)$-alkoxy, CN, OH, CHO, CH—$[(C_1-C_6)$-alkoxy$]_2$, COOH, $C(O)—O—(C_1-C_6)$-alkyl, $C(O)—O—(C_6-C_{12})$-aryl, $C(O)—(C_1-C_6)$-alkyl, $C(O)—(C_6-C_{12})$-aryl, $O—C(O)—(C_1-C_6)$-alkyl, $O—C(O)—(C_6-C_{12})$-aryl, $R^{12}$, $R^{13}$, $R^{14}$, $R^{15}$ and $R^{16}$ are identical to or independent of one another and are $(C_1-C_6)$-alkyl, $(C_6-C_{12})$-aryl, where alkyl and aryl are unsubstituted or substituted one or more times by fluorine, chlorine, bromine, $NO_2$, $NH_2$ or protected form, CN, OH, COOH, $(C_1-C_6)$-alkyl, $(C_1-C_6)$-alkoxy, $C(O)—O—(C_1-C_6)$-alkyl, $C(O)—O—(C_6-C_{12})$-aryl, $C(O)—(C_1-C_6)$-alkyl, $C(O)—(C_6-C_{12})$-aryl, $O—C(O)—(C_1-C_6)$-alkyl, $O—C(O)—(C_6-C_{12})$-aryl, $R^{17}$ is hydrogen, $(C_1-C_6)$-alkyl, where alkyl are unsubstituted or substituted one or more times by fluorine, chlorine, bromine, $NO_2$, $NH_2$ or protected form, CN, OH, COOH, $(C_1-C_6)$-alkyl, $(C_1-C_6)$-alkoxy, $C(O)—O—(C_1-C_6)$-alkyl, $C(O)—O—(C_6-C_{12})$-aryl, $C(O)—(C_1-C_6)$-alkyl, $C(O)—(C_6-C_{12})$-aryl, $O—C(O)—(C_1-C_6)$-alkyl, $O—C(O)—(C_6-C_{12})$-aryl, $R^{18}$ and $R^{19}$, identically to or independently of one another, are hydrogen, CN, $C(O)—O—(C_1-C_6)$-alkyl, $C(O)—O—(C_6-C_{12})$-aryl, $C(O)—(C_1-C_6)$-alkyl, $C(O)—(C_6-C_{12})$-aryl, where alkyl and aryl can be substituted one or more times by fluorine, chlorine, bromine, $NO_2$, $NH_2$ or protected form, CN, OH, COOH, $(C_1-C_6)$-alkyl, $(C_1-C_6)$-alkoxy, $C(O)—O—(C_1-C_6)$-alkyl, $C(O)—O—(C_6-C_{12})$-aryl, $C(O)—(C_1-C_6)$-alkyl, $C(O)—(C_6-C_{12})$-aryl $O—C(O)—(C_1-C_6)$-alkyl, $O—C(O)—(C_6-C_{12})$-aryl, with the proviso that for $R^{18}$=hydrogen, $R^{19}$ cannot also be hydrogen and vice vera, $R^{20}$ is hydrogen, $(C_1-C_{18})$-alkyl, $(C_2-C_{18})$-alkenyl, $(C_2-C_{18})$-alkynyl, $(C_6-C_{12})$-aryl, $(C_7-C_{20})$-arylalkyl, wherein alkyl, alkenyl, alkynyl and aryl can be substituted one or more times by fluorine, chlorine, bromine, $NO_2$, $NH_2$ or protected form, $(C_1-C_6)$-alkyl, $(C_1-C_6)$-alkoxy, CN, OH, CHO, CH—[$(C_1-C_6)$-alkoxy]$_2$, COOH, C(O)—O—$(C_1-C_6)$-alkyl, C(O)—O—$(C_6-C_{12})$-aryl, C(O)—$(C_1-C_6)$-alkyl, C(O)—$(C_6-C_{12})$-aryl, O—C(O)—$(C_1-C_6)$-alkyl, O—C(O)—$(C_6-C_{12})$-aryl, or wherein the carbon nucleophiles are organometallic compounds selected from the group consisting of $R^2{}_2Cu(CN)Li_2$, $R^2Li$, $R^2MgX$, $R^2ZnX$, $R^2{}_2Zn$ and $R^2{}_{4-n}TiR^{22}{}_n$ (n<4), where $R^2$ and $R^{22}$ have the abovementioned meanings and X is a leaving group.

7. The process as claimed in claim 1, wherein the base in the reaction of a compound of the formula IV is a tri-$(C_1-C_6)$-alkylamine, pyridine, butyllithium, lithium diisopropylamide (LDA), sodium hydride, sodium amide, potassium tert-butoxide, sodium amide-$R^{21}$ONa, $R^{21}$ being $(C_2-C_6)$-alkyl or $CH_3CH_2$—)—$CH_2CH_2$, or uncharged, peralkylated polyaminophosphazene bases.

8. The process of claim 7, wherein $R^{21}$ is a tri-$(C_1-C_3)$-alkylamine or pyridine.

* * * * *

UNITED STATES PATENT AND TRADEMARK OFFICE
CERTIFICATE OF CORRECTION

PATENT NO. : 5,608,098

DATED : March 04, 1997

INVENTOR(S) : Anuschirwan PEYMAN et al.

It is certified that error appears in the above-indentified patent and that said Letters Patent is hereby corrected as shown below:

Claim 1, column 15, line 11, after "with a base to", insert --form--.

Claim 1, column 15, line 33, "nTiR$^{22}$n" should read --$_n$TiR$^{22}_n$--.

Claim 1, column 15, line 34, "meaning;" should read --meaning,--.

Claim 1, column 15, line 40, after "(C$_1$-C$_6$)-alkyl" insert --,--.

Claim 6, column 16, line 47, "alkyl are" should read --alkyl is --.

Claim 6, column 16, line 58, "can be" should read --are unsubstituted or--.

Claim 6, column 16, line 63, after "C(0)-(C$_6$-C$_{12}$)-aryl", insert --,--.

UNITED STATES PATENT AND TRADEMARK OFFICE
CERTIFICATE OF CORRECTION

PATENT NO. : 5,608,098
DATED : March 04, 1997
INVENTOR(S) : Anuschirwan PEYMAN et al.

It is certified that error appears in the above-indentified patent and that said Letters Patent is hereby corrected as shown below:

Claim 6, column 16, line 66, "vera" should read --versa--.

Claim 6, column 18, line 1, "$nTiR^{22}{}_n$" should read --$_nTiR^{22}{}_n$--.

Signed and Sealed this

Second Day of December, 1997

BRUCE LEHMAN

Attest:

Attesting Officer

Commissioner of Patents and Trademarks